United States Patent
Ding et al.

(10) Patent No.: US 9,724,452 B2
(45) Date of Patent: Aug. 8, 2017

(54) DRUG DELIVERY SCAFFOLD OR STENT WITH A NOVOLIMUS AND LACTIDE BASED COATING SUCH THAT NOVOLIMUS HAS A MINIMUM AMOUNT OF BONDING TO THE COATING

(71) Applicant: Abbott Cardiovascular Systems Inc., Santa Clara, CA (US)

(72) Inventors: Ni Ding, San Jose, CA (US); Stephen Pacetti, San Jose, CA (US); Marika Kamberi, San Jose, CA (US); Cameron Kerrigan, Burlingame, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 0 days.

(21) Appl. No.: 15/161,084

(22) Filed: May 20, 2016

(65) Prior Publication Data

US 2016/0263293 A1    Sep. 15, 2016

Related U.S. Application Data

(62) Division of application No. 14/298,616, filed on Jun. 6, 2014, now Pat. No. 9,364,588.

(60) Provisional application No. 61/935,832, filed on Feb. 4, 2014.

(51) Int. Cl.
| | | |
|---|---|---|
| *A61L 31/10* | (2006.01) | |
| *A61L 31/16* | (2006.01) | |
| *A61L 31/14* | (2006.01) | |
| *A61K 47/48* | (2006.01) | |
| *A61K 31/436* | (2006.01) | |

(52) U.S. Cl.
CPC ............ *A61L 31/16* (2013.01); *A61K 31/436* (2013.01); *A61K 47/482* (2013.01); *A61K 47/48992* (2013.01); *A61L 31/10* (2013.01); *A61L 31/148* (2013.01); *A61L 2300/416* (2013.01); *A61L 2420/02* (2013.01)

(58) Field of Classification Search
CPC .... A61L 2420/02; A61L 31/148; C08L 67/04; A61K 47/48992
See application file for complete search history.

(56) References Cited

U.S. PATENT DOCUMENTS

2009/0285873 A1    11/2009  Lim et al.
2012/0271396 A1*   10/2012  Zheng ..................... A61F 2/82
                                                  623/1.2

* cited by examiner

Primary Examiner — Gregory Listvoyb
(74) Attorney, Agent, or Firm — Squire Patton Boggs (US) LLP

(57) ABSTRACT

Disclosed herein are drug delivery medical devices. A polymer coating for a medical device is provided which comprises a minimum amount of a drug bonded to the polymer in the coating.

19 Claims, 1 Drawing Sheet

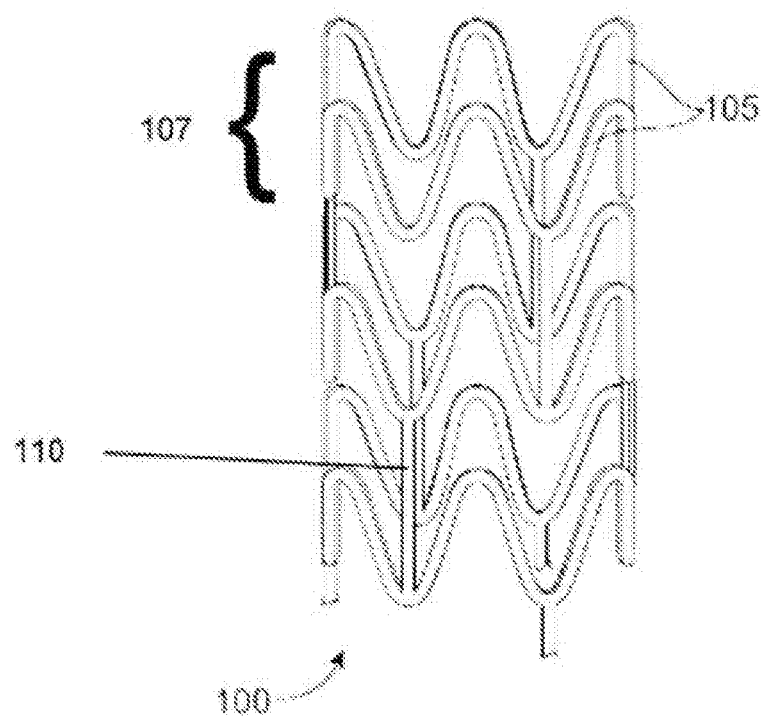

DRUG DELIVERY SCAFFOLD OR STENT WITH A NOVOLIMUS AND LACTIDE BASED COATING SUCH THAT NOVOLIMUS HAS A MINIMUM AMOUNT OF BONDING TO THE COATING

FIELD

Disclosed herein are drug delivery medical devices. More particularly, a polymer coating for a medical device is provided which comprises a minimum amount of a drug bonded to the polymer in the coating.

BACKGROUND

A majority of drug delivery stents and scaffolds include three components, (1) a scaffold/stent structure, substrate, or body, (2) a polymeric coating, and (3) a therapeutic agent typically present to reduce neointimal hyperplasia and restenosis. The primary purpose of the polymeric coating is to hold the drug on the scaffold and control its release rate. A bioresorbable scaffold includes a bioresorbable scaffold structure and a bioresorbable coating. Bioresorbable coatings are also placed on metallic stents with the goal of offering benefits compared to a permanent polymer coating.

As a drug/device combination product, drug delivery scaffolds must meet existing standards for drug release rate control and preservation of drug purity. An example of such a standard is the Q3B(R2) Impurities in New Drug Products standard, FDA July 2006. When a drug is mixed with a polymer it is possible for it to become chemically altered from reaction with the polymer itself, reaction with environmental species, or post packaging sterilization (such as terminal sterilization), among other mechanisms. Reaction of the drug with the carrier polymer, resulting in a drug that is conjugated to the coating polymer, is problematic as it both decreases the drug dose and generates new species with unknown biological and toxicological properties. Significant amounts of these species, where a significant level may be as low as 1%, necessitate complex and expensive studies to identify the new species and can require toxicological studies. Ultimately, substantial amounts of drug-polymer species can lead to studies resembling the regulatory path for a new drug substance, such as the US Food and Drug Administration (FDA) Investigational New Drug process (IND). This outcome can be prohibitively expensive and of little value, as drug degradation products and drug-polymer adducts rarely have any therapeutic value above that of the unaltered drug.

SUMMARY

Accordingly, provided herein are implantable devices, for example stents and bioabsorbable scaffolds, comprising a device body and a coating on the body, wherein the coating comprises a polymer (e.g., a PLA-based polymer) and a macrocyclic drug (e.g., novolimus) conjugated to the polymer, wherein the amount of the macrocyclic drug conjugated to the polymer is sufficiently low so as not to decrease the drug dose from the device and not to generate new species with unknown biological and/or toxicological properties.

In an embodiment, provided herein is an implantable device, for example a stent or a bioabsorbable scaffold, comprising a device body and a coating on the device body, the coating comprising a poly(D,L-lactide) (PDLLA) polymer and novolimus conjugated to the polymer, wherein the amount of novolimus conjugated to the polymer is less than or equal to 0.35% (weight novolimus to weight polymer), as measured by liquid chromatography-mass spectrometry (LC-MS).

In another embodiment, provided herein is an implantable device, for example a stent or a bioabsorbable scaffold, comprising a device body and a coating on the device body, the coating comprising a polymer, wherein the polymer comprises a lactide, lactide units, a lactic acid, or lactic acid units and novolimus conjugated to the lactide, lactide units, lactic acid, or lactic acid units, wherein the amount of novolimus conjugated to the polymer is less than or equal to 0.35% (weight novolimus to weight polymer), as measured by liquid chromatography-mass spectrometry (LC-MS).

In an embodiment, provided herein is a bioabsorbable scaffold comprising a scaffold body and a coating on the scaffold body, the coating comprising a polymer, wherein the polymer comprises a lactide or lactic acid based polymer and novolimus conjugated to the lactide or lactic acid based polymer, wherein the amount of novolimus conjugated to the polymer is less than or equal to 0.35% (weight novolimus to weight polymer), as measured by liquid chromatography-mass spectrometry (LC-MS).

BRIEF DESCRIPTION OF THE DRAWINGS

FIG. 1 depicts a view of an exemplary scaffold.

DETAILED DESCRIPTION

One rapamycin derivative which is used with a drug delivery implantable device described herein is novolimus. Preferred bioresorbable polymers which are used herein as a coating on an implantable device, such as a stent or bioabsorbable scaffold, in combination with novolimus, comprise poly(lactic acid) (PLA) based polymers. A PLA-based polymer can include a homopolymer or copolymer. A PLA-based copolymer, unless otherwise specified, can include an alternating copolymer, a periodic copolymer, a statistical copolymer, a random copolymer, a block copolymer, a graft copolymer, a crosslinked copolymer, and/or a stereoblock copolymer. A PLA-based polymer can include, unless otherwise specified, two, three, four, or more different types of repeating monomer, oligomer, or polymer units.

Reaction between a rapamycin derivative, such as novolimus, and a PLA-based polymer is possible as PLA-based polymers have reactive endgroups. For PLA-based polymers synthesized by ring-opening polymerization, one terminus of the polymer is a hydroxyl group. In addition, any polymer degradation during manufacturing and sterilization can lead to carboxylic acid endgroups and additional hydroxyl endgroups. Polylactic acid polymers have a carboxylic acid endgroup and a hydroxyl endgroup. Novolimus has four hydroxyl groups and these can couple with carboxylic acid endgroups of PLA, coupling the drug to the polymer. Additionally, novolimus comprises an ester group, and this can couple via trans esterification with the hydroxyl end group of a PLA polymer, coupling the drug to the polymer. This later reaction opens the macrocyclic lactone ring of the drug.

Accordingly, provided herein are implantable devices, for example stents and bioabsorbable scaffolds, comprising a device body and a coating on the device body, wherein the coating comprises a polymer and a macrocyclic drug conjugated to the polymer, wherein the amount of the macrocyclic drug conjugated to the polymer is sufficiently low so as not to decrease the drug dose from the device and not to generate new species, or impurities, with unknown biological and/or toxicological properties. The drug dose per mm of device length may be 2 to 3 micrograms (mcg), 3 to 4 mcg, 4 to 5 mcg, 5 to 6 mcg, 6 to 8 mcg, 3 mcg, 4 mcg, 5 mcg, 6 mcg, 7 mcg, 8 mcg, or 9 mcg. The implantable device body itself and/or the polymer of the coating may be any one of, or combination of, poly(lactic acid) or poly(lactide) ("PLA") based polymers.

Drugs for Conjugation

A wide range of drugs, for example macrocyclic drugs, can be used with the drug delivery medical devices and polymers described herein. As used herein, and unless otherwise specified, the term "macrocyclic drug" refers to a macrocyclic lactone chemical species which is a derivative, metabolite, or otherwise has a chemical structure similar to that of sirolimus and is useful for the treatment of neointimal hyperplasia, restenosis, and/or other vascular conditions, such as vulnerable plaque. Examples of "macrocyclic drugs" include biolimus, merilimus, myolimus, novolimus, pimecrolimus, 16-pent-2-ynyloxy-32(S)-dihydro-rapamycin, ridaforolimus, tacrolimus, temsirolimus and zotarolimus. In an embodiment of the compounds, compositions, devices and methods provided herein, the macrocyclic drug is novolimus.

Other drugs useful for the treatment of neointimal hyperplasia, restenosis, and/or other vascular conditions, such as vulnerable plaque, can be used with the drug delivery medical devices and polymers described herein. Such drugs include those having ester groups and/or pendant hydroxyl groups, such as paclitaxel which has pendant hydroxyl groups.

In a preferred embodiment, the drugs are in an amorphous form when conjugated to the polymer of the drug delivery device.

As used herein, and unless otherwise specified, the terms "rapamycin" and "sirolimus" are used interchangeably and refer to the compound having the following chemical structure and systematic (IUPAC) name:

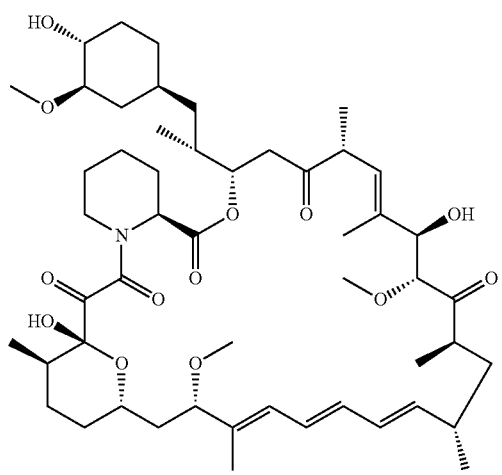 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

(3S, 6R, 7E, 9R, 10R, 12R, 14S, 15E, 17E, 19E, 21S, 23S, 26R, 27R, 34aS)-9, 10, 12, 13, 14, 21, 22, 23, 24, 25, 26, 27, 32, 33, 34, 34a-hexadecahydro-9, 27-dihydroxy-3-[(1R)-2-[(1S,3R,4R)-4-hydroxy-3-methoxycyclohexyl]-1-methylethyl]-10, 21-dimethoxy-6, 8, 12, 14, 20, 26-hexamethyl-23, 27-epoxy-3H-pyrido[2, 1-c][1, 4]-oxaazacyclohentriacontine-1, 5, 11, 28, 29(4H, 6H, 31H)-pentone "Rapamycin" can also be identified by the following tradenames: Antibiotic AY 22989, AY 22989, AY-22989, CCRIS 9024, HSDB 7284, NSC 226080, Rapammune, Rapamune, SILA 9268A, UNII-W36ZG6FT64, and WY-090217. "Rapamycin" can also be identified by the Chemical Abstracts Service registry number 53123-88-9. "Rapamycin" is also described in the following references which are each expressly incorporated herein by reference: U.S. Pat. No. 5,100,899 A; Sehgal, et al., *The Journal of Antibiotics*, vol. 28 (1975), no. 10, pp. 727-732; and Swindells, et al., *The Canadian Journal of Chemistry*, vol. 56 (1978), pp. 2491-2492.

As used herein, and unless otherwise specified, the term "novolimus" refers to the compound having the following chemical structure and name:

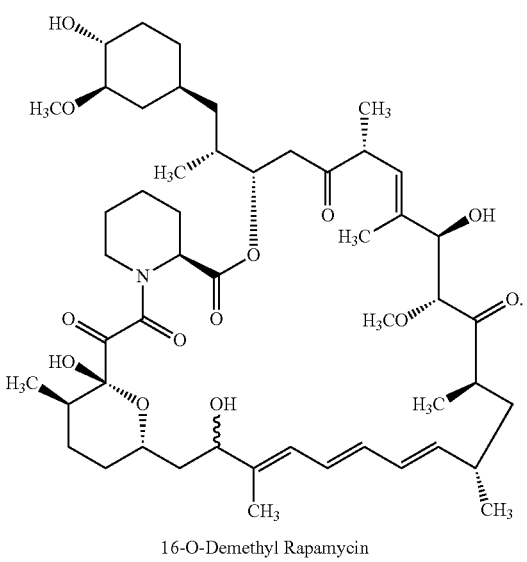

16-O-Demethyl Rapamycin

"Novolimus" can also be identified by 7-O-Demethyl Rapamycin and by the Chemical Abstracts Service registry number 151519-50-5. "Novolimus" is described in the following references, which are expressly incorporated herein by reference: U.S. Pat. No. 7,867,988 B2; U.S. Pat. No. 8,367,081 B2; and U.S. Pat. No. 8,404,641 B2.

As used herein, and unless otherwise specified, the term "biolimus" refers to the compound having the following chemical structure and name:

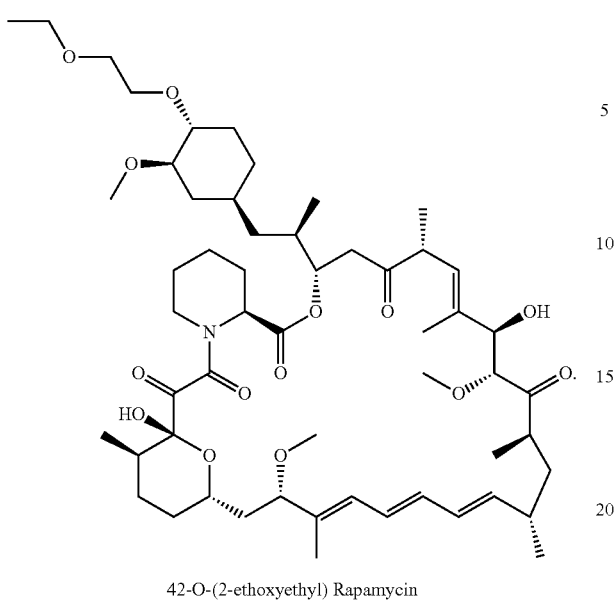

42-O-(2-ethoxyethyl) Rapamycin

"Biolimus" can also be identified by: Biolimus A9, Umirolimus, A9, Ba9, TRM-986, and UNII-U36PGF65JH; and by the Chemical Abstracts Service registry number 851536-75-9. "Biolimus" is described in U.S. Pat. No. 7,220,755 B2, which is expressly incorporated herein by reference.

As used herein, and unless otherwise specified, the term "merilimus" refers to any of the following compounds: 42-O-(tetrahydrofuran-3-yl)rapamycin(Merilimus-1); 42-O-(oxetan-3-yl)rapamycin(Merilimus-2); 42-O-(tetrahydropyran-3-yl)rapamycin(Merilimus-3); 42-O-(4-methyl, tetrahydrofuran-3-yl) rapamycin; 42-O-(2,5,5-trimethyl, tetrahydrofuran-3-yl) rapamycin; 42-O-(2,5-diethyl-2-methyl, tetrahydrofuran-3-yl) rapamycin; 42-O-(2H-Pyran-3-yl, tetrahydro-6-methoxy-2-methyl) rapamycin, or 42-O-(2H-Pyran-3-yl, tetrahydro-2,2-dimethyl-6-phenyl) rapamycin. The chemical structures of 42-O-(tetrahydrofuran-3-yl) rapamycin (Merilimus-1), 42-O-(oxetan-3-yl) rapamycin(Merilimus-2), and 42-O-(tetrahydropyran-3-yl)rapamycin(Merilimus-3) are provided below:

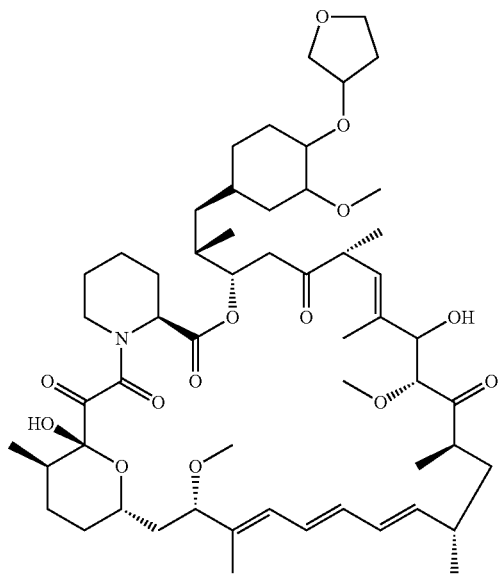

42-O-(tetrahydrofuran-3-yl) rapamycin
(Merilimus-1)

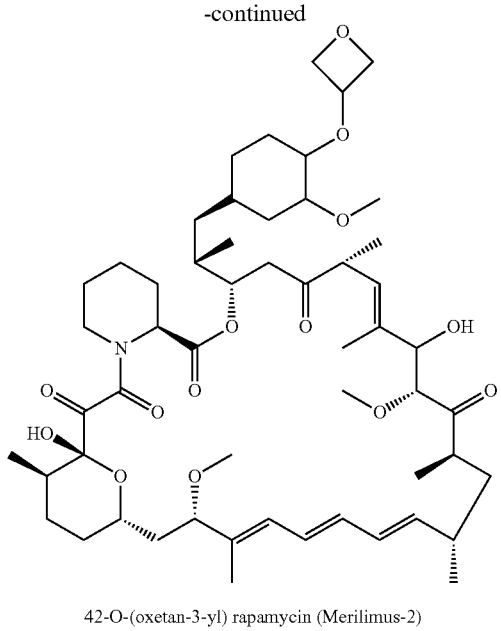

42-O-(oxetan-3-yl) rapamycin (Merilimus-2)

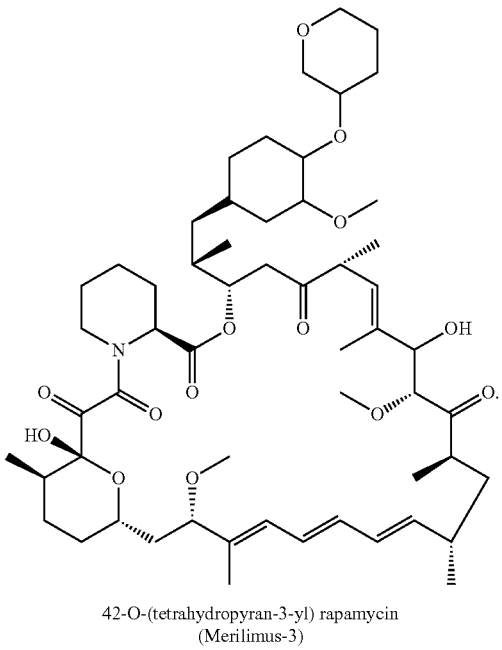

42-O-(tetrahydropyran-3-yl) rapamycin
(Merilimus-3)

"Merilimus" is described in U.S. Pat. Appl. Pub. No. US 2013/0184305 A1, which is expressly incorporated herein by reference.

As used herein, and unless otherwise specified, the term "myolimus" refers to the compound having the following chemical structure and name:

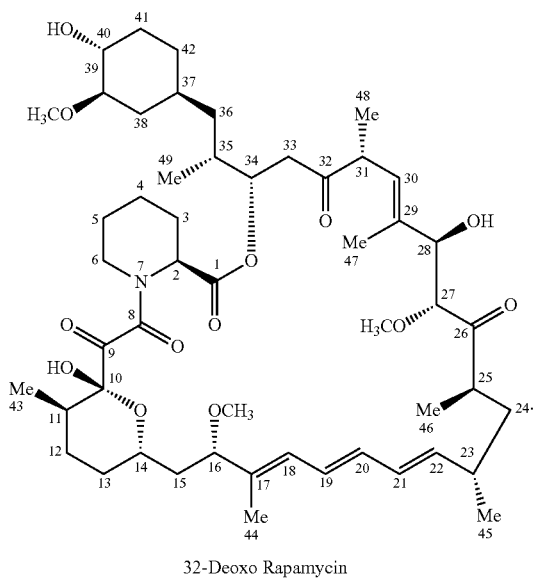

32-Deoxo Rapamycin

"Myolimus" can also be identified by: SAR943, SAR943-NXA, SAR943N, SDZ 227-943 N, UNII-IGL4DTS8F8, 32-deoxorapamycin, and olcorolimus; and by the Chemical Abstracts Service registry number 186752-78-3. "Myolimus" is described in the following references, which are expressly incorporated herein by reference: U.S. Pat. Appl. Pub. Nos. US 2010/0086579 A1; and US 2005/0020614 A1; and U.S. Pat. No. 5,985,890 A; and U.S. Pat. No. 6,200,985 B1.

As used herein, and unless otherwise specified, the term "paclitaxel" refers to the compound having the following chemical structure and name:

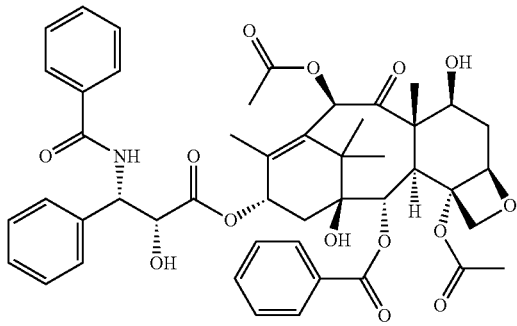 [SMILES: CC(=O)O[C@H]1C(=O)[C@@]2(C)[C@H]([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O]

Benzenepropanoic acid, beta-(benzoylamino)-alpha-hydroxy-, (2aR, 4S, 4aS, 6R, 9S, 11S, 12S, 12aR, 12bS)-6,12b-bis(acetyloxy)-12-(benzoyloxy)-2a,3,4, 4a,5,6,9,10,11,12,12a,12b-dodecahydro-4,11-dihydroxy-4a,8,13,13-tetramethyl-5-oxo-7,11-methano-1H-cyclodeca(3,4)benz(1,2-b)oxet-9-yl ester, (alphaR, betaS)—

"Paclitaxel" can also be identified by: (2aR,4S,4aS,6R,9S,11S,12S,12aR,12bS)-1,2a,3,4,4a,6,9,10,11,12,12a,12b-Dodecahydro4,6,9,11,12,12b-hexahydroxy-4a,8,13,13-tetramethyl-7,11-methano-5H-cyclodeca(3,4)benz(1,2-b)oxet-5-one 6,12b-diacetate, 12-benzoate, 9-ester with (2R,3S)—N-benzoyl-3-phenylisoserine; (2aR-(2aalpha, 4beta, 4abeta, 6beta, 9alpha(alpha R*, betaS*), 11alpha, 12alpha, 12balpha))-beta(Benzoylamino)-alpha-hydroxybenzenepropanoic acid 6,12b-bis(acetyloxy)-12-(benzoyloxy)-2a, 3, 4, 4a, 5, 6, 9, 10, 11, 12, 12a, 12b-dodecahydro-4a,8,13,13-tetramethyl-5-oxo-7,11-methano-1H-cyclodeca(3,4)benz(1,2-b)oxet-9-yl ester; (NAB)-Paclitaxel; 5beta,20-Epoxy-1,2-alpha, 4,7beta, 10beta, 13alpha-hexahydroxytax-11-en-9-one 4,10-diacetate 2-benzoate 13-ester with (2R,3S)—N-benzoyl-3-phenylisoserine; ABI 007; ABI-007; Abraxane; Abraxane I.V. Suspension; BMS 181339-01; BMS-181339-01; Capxol; CCRIS 8143; Cyclopax; DRG-0190; Ebetaxel; EndoTAG 1; Genetaxyl; Genexol; HSDB 6839; Intaxel; LipoPac; MBT 0206; Mitotax; Nab-paclitaxel; Nanoparticle albumin bound paclitaxel; NK 105; NSC 125973; NSC-125973; OncoGel; Onxol; Paclitaxel; Paxceed; Paxene; Plaxicel; QW 8184; TaxAlbin; Taxol; Taxol A; Taxus Liberte; Taxus stent; UNII-P88XT4IS4D; Yewtaxan; and Zisu; and by the Chemical Abstracts Service registry number 33069-62-4. "Paclitaxel" is described in the following reference, which is expressly incorporated herein by reference: Wani et al., *Plant antitumor agents. VI. Isolation and structure of taxol, a novel antileukemic and antitumor agent from Taxus brevifolia*, Journal of the American Chemical Society, (1971) vol. 93, no. 9, pp 2325-2327.

As used herein, and unless otherwise specified, the term "pimecrolimus" refers to the compound having the following chemical structure and name:

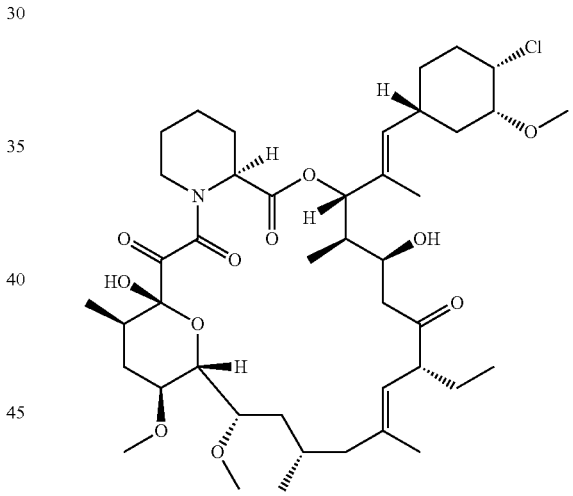

(3S,4R,5S,8R,9E,12S,14S,15R,16S,18R,19R,26aS)-3-((E)-2-((1R,3R,4S)-4-chloro-3 methoxycyclohexyl)-1-methylvinyl)-8-ethyl 5,6,8,11,12,13,14,15, 16,17,18,19,24,26, 26ahexadecahydro-5,19-epoxy-3H-pyrido(2,1-c)(1,4)oxaazacyclotricosine-1,17,20, 21(4H, 23H)-tetrone 33-epi-Chloro-33-desoxyascomycin "Pimecrolimus" can also be identified by: Elidel; SDZ ASM 981; SDZ-ASM 981; and UNIT-7KYV510875; and by the Chemical Abstracts Service registry number 137071-32-0. "Pimecrolimus" is described in U.S. Pat. No. 6,423,722 B1, which is expressly incorporated herein by reference.

As used herein, and unless otherwise specified, the term "16-pent-2-ynyloxy-32(S)-dihydro-Rapamycin" refers to the compound having the following chemical structure and name:

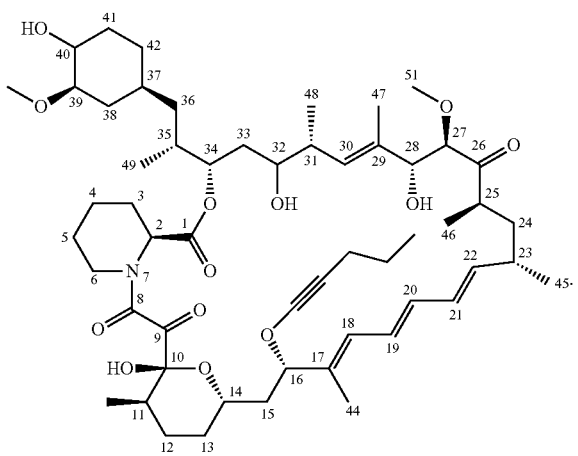

16-pent-2-ynyloxy-32(S)-dihydro-Rapamycin

"16-pent-2-ynyloxy-32(S)-dihydro-Rapamycin" is described in the following references, which are expressly incorporated herein by reference: U.S. Pat. No. 6,004,973 A; and U.S. Pat. No. 6,200,985 B1.

As used herein, and unless otherwise specified, the term "ridaforolimus" refers to the compound having the following chemical structure and name:

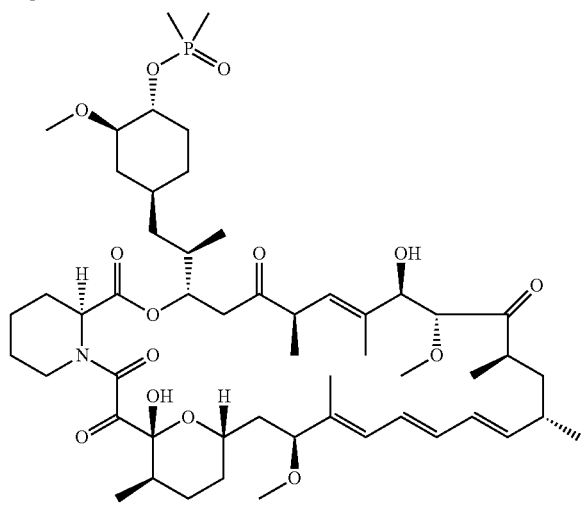 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OP(C)(C)=O)[C@H](OC)C2)CC(=O)[C@H](C)/C=C(\C)[C@@H](O)[C@@H](OC)C(=O)[C@H](C)C[C@H](C)/C=C/C=C/C=C/1C]

(1R,9S,12S,15R,16E,18R,19R,21R,23S,24E,26E, 28E,30S,32S,35R)-12-((1R)-2-((1S,3R,4R)-4-((Dimethylphosphinoyl)oxy)-3-methoxycyclohexyl)-1-methylethyl)-1,18-dihydroxy-19,30-dimethoxy5,17, 21,23,29,35-hexamethyl-11,36-dioxa-4-azatricyclo (30.3.1.04,9)hexatriaconta-16,24,26,28-tetraene-2,3, 10,14,20-pentone "Ridaforolimus" can also be identified by: AP 23573; AP23573; Deforolimus; MK 8669; MK-8669; MK8669; Taltorvic; UNII-48Z35KB15K; and 42-(dimethylphosphinate) Rapamycin; and by the Chemical Abstracts Service registry number 572924-54-0. "Ridaforolimus" is described in the following references, which are expressly incorporated herein by reference: U.S. Pat. No. 8,058,426 B2; U.S. Pat. No. 7,709,020 B2; U.S. Pat. No. 7,186,826 B2; and U.S. Pat. No. 7,091,213 B2.

As used herein, and unless otherwise specified, the term "tacrolimus" refers to the compound having the following chemical structure and name:

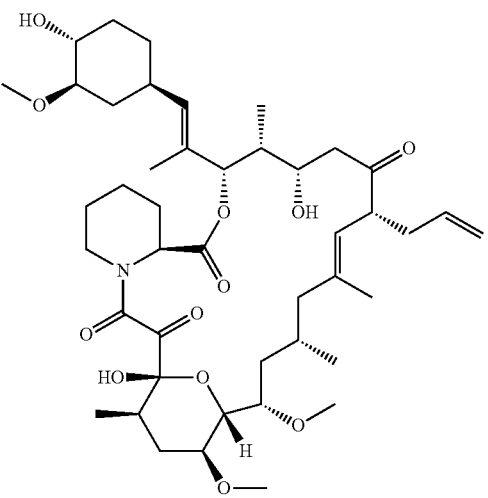 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

15,19-Epoxy-3H-pyrido(2,1-c)(1,4)oxaazacyclotricosine-1,7,20,21(4H,23H)-tetrone, 5,6,8,11,12,13, 14,15,16,17,18,19,24,25,26,26a-hexadecahydro-5, 19-dihydroxy-3-(2-(4-hydroxy-3-methoxycyclohexyl)-14,16-dimethoxy-4,10,12,18-tetramethyl-8-(2-propenyl)-, (3S-(3R*(E(1S*,3S*, 4S*)), 4S*,5R*,8S*,9E,12R*,14R*,15S*,16R*, 18S*,19S*,26aR*))-FK506

"Tacrolimus" can also be identified by: (−)-FK 506; Advagraf; Anhydrous tacrolimus; Astagraf XL; Avagraf; CCRIS 7124; Envarsus; FK 506; FK506; FR 900506; Fujimycin; L 679934; LCP-Tacro; Modigraf; Prograf; Prograft; Protopic; Protopy; Tsukubaenolide; and UNII-Y5L2157C4J; and by the Chemical Abstracts Service registry number 104987-11-3. "Tacrolimus" is described in the following references, which are expressly incorporated herein by reference: U.S. Pat. No. 5,665,727 A; U.S. Pat. No. 5,912,238 A; and U.S. Pat. No. 8,187,320 B2.

As used herein, and unless otherwise specified, the term "temsirolimus" refers to the compound having the following chemical structure and name:

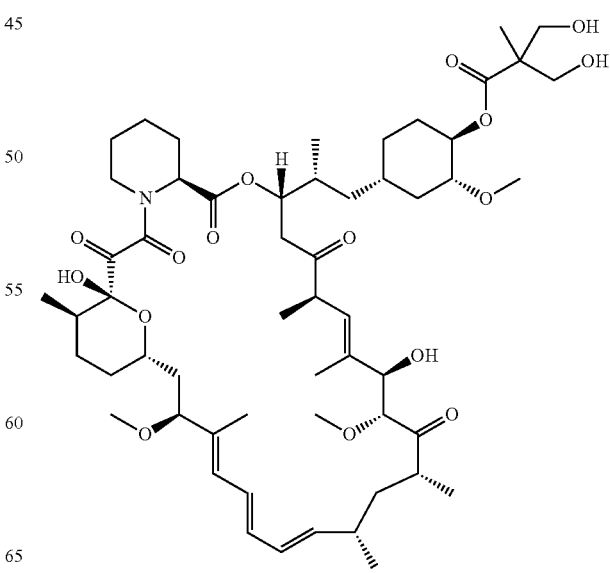

(3S,6R,7E,9R,10R,12R,14S,15E,17E,19E,21S,23S, 26R,27R,34aS)-9,10,12,13,14,21,22,23,24,25, 26,27, 32,33,34,34aHexadecahydro-9,27-dihydroxy-3- ((1R)-2-((1S,3R,4R)-4-hydroxy-3- methoxycyclohexyl)-1-methylethyl)-10,21- dimethoxy-6,8,12,14,20,26-hexamethyl-23,27- epoxy-3H-pyrido(2,1-c)(1,4) oxaazacyclohentriacontine-1,5,11,28,29(4H,6H, 31H)-pentone 4'-(2,2-bis(hydroxymethyl) propionate)

"Temsirolimus" can also be identified by: CCI 779; CCI-779; HSDB 7931; Rapamycin 42-(2,2-bis(hydroxymethyl) propionate); Torisel; UNII-624KN6GM2T; WAY-CCI 779; and 42-(3-hydroxy-2-(hydroxymethyl)-2-methylpropano-ate) Rapamycin; and by the Chemical Abstracts Service registry number 162635-04-3. "Temsirolimus" is described in U.S. Pat. No. 5,362,718 A, which is expressly incorporated herein by reference.

As used herein, and unless otherwise specified, the term "zotarolimus" refers to the compound having the following chemical structure and name:

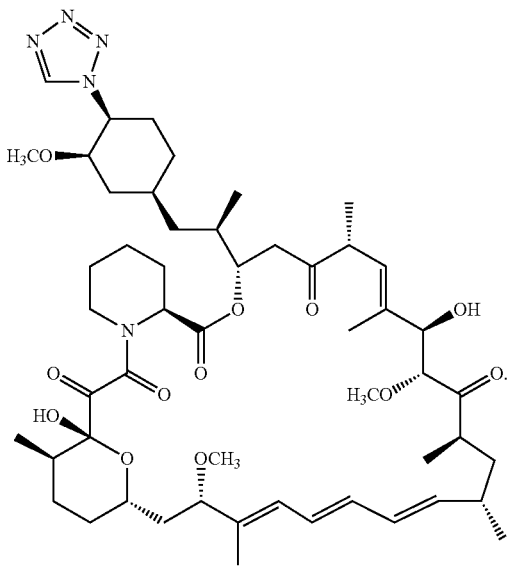

42-deoxy-42-(1H-tetrazol-1-yl)-, (42S)-Rapamycin

"Zotarolimus" can also be identified by: A 179578; ABT 578; ABT-578; and UNIT-H4GXR80IZE; and by the Chemical Abstracts Service registry number 221877-54-9.

Polymers

As used herein, and unless otherwise specified, the terms "polymer" and "polymeric" refer to compounds that are the product of a polymerization reaction. These terms are inclusive of homopolymers (i.e., polymers obtained by polymerizing one type of monomer), copolymers (i.e., polymers obtained by polymerizing two or more different types of monomers), terpolymers, etc., including random, alternating, block, graft, dendritic, crosslinked, and any other variations of polymers.

A wide range of polymers, for example polymers comprising poly(lactic acid) or poly(lactide), can be used with the drug delivery medical devices and drugs described herein. In an embodiment, the medical device body or scaffold, for example a stent, can be made from and/or coated with a polymer described herein, for example a polymer comprising poly(lactic acid) or poly(lactide), or a polymer comprising lactic acid, lactic acid units, lactide, or lactide units. In an embodiment, the polymer is a lactide or lactic acid polymer which comprises poly(lactic acid) or poly(lactide) ("PLA"). In an embodiment, a lactide or lactic acid polymer can be a polymer comprising L-lactide. In an embodiment, a lactide or lactic acid polymer can be a polymer comprising D-lactide. In one embodiment, a lactide or lactic acid polymer can be a polymer which incorporates at least 5% (w/w) of L-lactic acid or D-lactic acid.

A PLA-based polymer can include a homopolymer or copolymer. A PLA-based copolymer, unless otherwise specified, can include an alternating copolymer, a periodic copolymer, a statistical copolymer, a random copolymer, a block copolymer, a graft copolymer, a crosslinked copolymer, and/or a stereoblock copolymer. A PLA-based polymer can include, unless otherwise specified, two, three, four, or more different types of repeating monomer, oligomer, and/or polymer units.

Poly(lactic acid) based polymers (PLA-based polymers), useful for making and/or coating implantable devices, include poly(L-lactide), poly(D-lactide), poly(D,L-lactide), poly(D,L-lactide) having a constitutional unit weight-to-weight (wt/wt) ratio of about 96/4, poly(L-lactide-co-D,L-lactide), poly(L-lactide-co-glycolide), poly(D,L-lactide-co-glycolide), poly(L-lactide-co-caprolactone), poly(D,L-lactide-co-caprolactone), poly(D,L-lactide) made from meso-lactide, and poly(D,L-lactide) made from polymerization of a racemic mixture of L- and D-lactides. In an embodiment, the poly(lactic acid) based polymers (PLA-based polymers) include poly(D,L-lactide) having a constitutional unit weight-to-weight (wt/wt) ratio of about 93/7, about 94/6, about 95/5, about 96/4, about 97/3, about 98/2, or about 99/1. The caprolactone copolymers may have 1 to 5 wt % caprolactone units. The coating polymer may also be a blend of any combination of the polymers described herein. The coating polymer may also be a blend of a PLA-based polymer and polycaprolactone with about 1 to 5 wt % of polycaprolactone. The term "constitutional unit" refers to the composition of a monomer as it appears in a polymer.

The coating polymer can also be a blend of a PLA-based polymer and other biocompatible polymers known in the art. The polymer can comprise a copolymer of lactide and glycolide. In an embodiment, the polymer comprises a poly(L-lactide-co-glycolide) copolymer. In an embodiment, the poly(L-lactide-co-glycolide) copolymer is amorphous. In an embodiment, the poly(L-lactide-co-glycolide) copolymer is 85% lactide and 15% glycolide. In an embodiment, the polymer is an amorphous poly(L-lactide-co-glycolide) copolymer comprising 85% lactide and 15% glycolide. In an embodiment, the polymer comprises a poly(D-lactide-co-glycolide) copolymer. In an embodiment, the poly(D-lactide-co-glycolide) copolymer is amorphous. In an embodiment, the poly(D-lactide-co-glycolide) copolymer is 85% lactide and 15% glycolide. In an embodiment, the polymer is an amorphous poly(D-lactide-co-glycolide) copolymer comprising 85% lactide and 15% glycolide. In an embodiment, the polymer comprises a poly(D,L-lactide-co-glycolide) copolymer. In an embodiment, the poly(D,L-lactide-co-glycolide) copolymer is amorphous. In an embodiment, the poly(D,L-lactide-co-glycolide) copolymer is 85% lactide and 15% glycolide. In an embodiment, the polymer is an amorphous poly(D,L-lactide-co-glycolide) copolymer comprising 85% lactide and 15% glycolide.

In an embodiment, the polymer comprises poly(D,L-lactide), poly(lactide-co-glycolide), polylactide-co-polycaprolactone, poly(L-lactide-co-trimethylene carbonate), polytrimethylene carbonate or copolymers thereof, polyorthoesters or copolymers thereof, polyanhydrides or copolymers thereof, polylactide or copolymers thereof, polyglycolides or copolymers thereof, polycaprolactone or copolymers thereof, or polyiminocarbonates or copolymers thereof.

In an embodiment, the glass transition temperature ($T_g$) of the PLA-based polymer is selected over the range of 40° C. to 65° C. In one embodiment, the PLA-based polymer comprises poly(D,L-lactide) and the glass transition temperature ($T_g$) is selected over the range of 55° C. to 62° C.

In an embodiment, the crystalline melting temperature ($T_m$) of the PLA-based polymer is selected over the range of 155° C. to 195° C. In one embodiment, the PLA-based polymer comprises poly(D,L-lactide) and the crystalline melting temperature ($T_m$) is selected over the range of 155° C. to 195° C.

In an embodiment, the number average molecular weight ($M_n$) of the PLA-based polymer is selected over the range of 20,000 daltons (Da) to 500,000 Da. In one embodiment, the $M_n$ of the PLA-based polymer is selected over the range of 20,000 Da to 60,000 Da. In one embodiment, the PLA-based polymer comprises poly(D,L-lactide) and the $M_n$ is selected over the range of 20,000 Da to 500,000 Da. In one embodiment, the PLA-based polymer comprises poly(D,L-lactide) and the $M_n$ is selected over the range of 20,000 Da to 60,000 Da.

In an embodiment, the weight average molecular weight ($M_w$) of the PLA-based polymer is selected over the range of 30,000 Da to 1,000,000 Da. In one embodiment, the PLA-based polymer comprises poly(D,L-lactide) and the weight average molecular weight ($M_w$) is selected over the range of 30,000 Da to 1,000,000 Da. In an embodiment of the devices and methods described herein, a PLA-based polymer coating comprises poly(D,L-lactide) having a number average molecular weight ($M_n$) selected over the range of 20,000 Da to 60,000 Da.

Polymer-Drug Conjugates

In purely chemical terms, conjugation can indicate the covalent bonding of the drug to the polymer. This bond may be between the drug and a polymer endgroup or it can be between the drug and a functional group along the polymer backbone. Other forms of chemical bonding are possible. The drug can, for example, be ionically bound to the polymer. This typically requires permanent charges on the drug and polymer. Chelation via chelating moieties may use coordination bonds with polydentate moieties. Lewis acid or dative bonding may associate the drug strongly with the polymer. Hydrogen bonding may result is a strong interaction between drug and polymer if multiple hydrogen bonds are present. Criteria for the binding, associating, conjugation, or bonding of the drug to the polymer would be:

Evidence via chemical means known to those in the art that the molecules are conjugated, such as by mass spectrometry (MS), liquid chromatography-mass spectrometry (LC-MS), nuclear magnetic resonance spectrometry (NMR), and/or gel permeation chromatography with refractive index and ultraviolet detection (GPC-RI/UV);

Evidence that the drug and polymer remain together when dissolved in an appropriate solvent; and/or Evidence that the two species co-elute in a chromatographic method when the two unreacted species have different retention times.

A drug having a pendant hydroxyl group, such as novolimus, can be conjugated to a PLA-based polymer. Conjugation of the two, optionally with added acid catalyst and heat, can create an ester bond between the species, as shown in the scheme below:

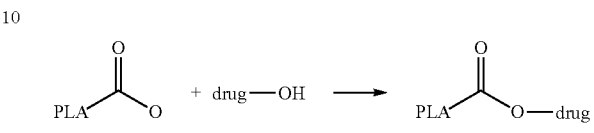

Novolimus, for example, can react with the carboxylic acid end group of a PLA polymer via one of the four novolimus hydroxyl groups. Conjugation of PLA and novolimus, optionally with added acid catalyst and heat, can create an ester bond between the species, as shown in the scheme below:

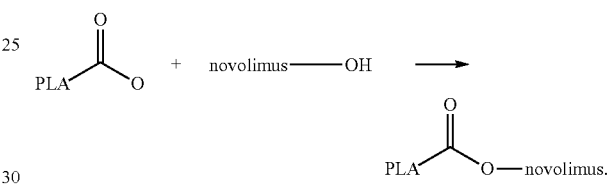

The above reaction can be carried out by methods know to those of skill in the art and the PLA polymer tested for an amount of drug-polymer conjugate sufficiently low so as not to decrease the drug dose from the polymer and not to generate new species with unknown biological and/or toxicological properties.

Drug-Polymer Conjugate Detection

The amount of drug-polymer conjugate can be measured by standard methods known in the art. In an embodiment, the amount of drug-polymer conjugate is measured by mass spectrometry (MS), liquid chromatography-mass spectrometry (LC-MS), nuclear magnetic resonance spectrometry (NMR), and/or gel permeation chromatography with refractive index and ultraviolet detection (GPC-RI/UV).

Gel permeation chromatography (GPC) separates analytes based on size or hydrodynamic volume. Separation is by use of porous beads packed in a column. There is a limited range of molecular weights that can be separated by each column and therefore the size of the pores for the packing is chosen according to the range of molecular weight of analytes to be separated. For polymer separations the pore sizes is on the order of the size of the polymer molecules in solution being analyzed. If a sample has a broad molecular weight range, several GPC columns can be used in tandem to fully resolve the sample. For GPC-RI/UV, samples are dissolved in tetrahydrofuran (THF) and analyzed by gel permeation chromatography (GPC) with refractive index (RI) detection and ultraviolet (UV) detection in series.

Liquid chromatography-mass spectrometry (LC-MS) combines the physical separation of liquid chromatography (including high performance liquid chromatography) with the mass analysis of mass spectrometry (MS). LC-MS has high sensitivity and selectivity and is useful for separation, detection and identification of chemicals, including drug-polymer conjugates, including in complex mixtures.

Detection of the amount of drug-polymer conjugate can include detection of drug-monomer, drug-dimer, and drug-oligomer conjugates by mass spectrometry (MS), liquid chromatography-mass spectrometry (LC-MS), nuclear magnetic resonance spectrometry (NMR), and/or gel permeation chromatography with refractive index and ultraviolet detection (GPC-RI/UV). Detected amounts of drug-monomer, drug-dimer, and drug-oligomer conjugates can be indicative of the amount of drug-polymer conjugate in a coating. For example, for certain detection methods and protocols, the amount of drug-monomer, drug-dimer, and/or drug-oligomer conjugates detected from a coating sample can be correlated to an amount of drug-polymer conjugate in the coating.

As used herein, the term "drug-monomer conjugate," unless otherwise stated, refers to a conjugate having a drug conjugated to a monomer unit of a polymer described herein.

As used herein, the term "drug-dimer conjugate," unless otherwise stated, refers to a conjugate having a drug conjugated to two monomer units of a polymer described herein.

As used herein, the term "drug-oligomer conjugate," unless otherwise stated, refers to a conjugate having a drug conjugated to two or more monomer units of a polymer described herein. In an embodiment, a "drug-oligomer conjugate" refers to a conjugate having a drug conjugated to from 2 to 100, 2 to 50, or 2 to 10 monomer units of a polymer described herein.

Modern chemical analytical techniques, especially those utilizing mass spectrometry detection, have low lower limits of detection. In an embodiment, the lower limit of detection of the method used to measure the amount of drug-polymer conjugate is less than 0.01%. In an embodiment, the lower limit of detection is less than 0.02%. In an embodiment, the lower limit of detection is less than 0.05%. In an embodiment, the lower limit of detection is less than 0.1%. In an embodiment, the method used to measure the amount of drug-polymer conjugate is liquid chromatography-mass spectrometry (LC-MS). In an embodiment, the method used to measure the amount of drug-polymer conjugate is gel permeation chromatography with refractive index and ultraviolet detection (GPC-RI/UV).

Low levels of drug-polymer conjugate are desired. In an embodiment, the amount of drug-polymer conjugate is less than or equal to 2 wt % of the drug polymer mixture, preferably less than or equal to 1 wt % of the drug polymer mixture. In an embodiment, the amount of drug-polymer conjugate is less than or equal to 0.50 wt % of the drug polymer mixture. In an embodiment, the amount of drug-polymer conjugate is less than or equal to 0.40 wt % of the drug polymer mixture. In a preferred embodiment, the amount of drug-polymer conjugate is less than or equal to 0.35 wt % of the drug polymer mixture. In a more preferred embodiment, the amount of drug-polymer conjugate is less than or equal to 0.30 wt % of the drug polymer mixture. In an embodiment, the amount of drug-polymer conjugate is less than or equal to 0.29 wt % of the drug polymer mixture.

In an embodiment, the amount of drug-polymer conjugate is greater than 0.01 wt % and less than or equal to 1 wt % or 2 wt %. In an embodiment, the amount of drug-polymer conjugate is greater than 0.01 wt % and less than or equal to 0.50 wt %. In an embodiment, the amount of drug-polymer conjugate is greater than 0.01 wt % and less than or equal to 0.40 wt %. In an embodiment, the amount of drug-polymer conjugate is greater than 0.01 wt % and less than or equal to 0.35 wt %. In an embodiment, the amount of drug-polymer conjugate is greater than 0.01 wt % and less than or equal to 0.30 wt %. In an embodiment, the amount of drug-polymer conjugate is greater than 0.01 wt % and less than or equal to 0.29 wt %.

In an embodiment, the amount of drug-polymer conjugate is greater than 0.02 wt % and less than or equal to 1 wt % or 2 wt %. In an embodiment, the amount of drug-polymer conjugate is greater than 0.02 wt % and less than or equal to 0.50 wt %. In an embodiment, the amount of drug-polymer conjugate is greater than 0.02 wt % and less than or equal to 0.40 wt %. In an embodiment, the amount of drug-polymer conjugate is greater than 0.02 wt % and less than or equal to 0.35 wt %. In an embodiment, the amount of drug-polymer conjugate is greater than 0.02 wt % and less than or equal to 0.30 wt %. In an embodiment, the amount of drug-polymer conjugate is greater than 0.02 wt % and less than or equal to 0.29 wt %.

In an embodiment, the amount of drug-polymer conjugate is greater than 0.05 wt % and less than or equal to 1 wt % or 2 wt %. In an embodiment, the amount of drug-polymer conjugate is greater than 0.05 wt % and less than or equal to 0.50 wt %. In an embodiment, the amount of drug-polymer conjugate is greater than 0.05 wt % and less than or equal to 0.40 wt %. In an embodiment, the amount of drug-polymer conjugate is greater than 0.05 wt % and less than or equal to 0.35 wt %. In an embodiment, the amount of drug-polymer conjugate is greater than 0.05 wt % and less than or equal to 0.30 wt %. In an embodiment, the amount of drug-polymer conjugate is greater than 0.05 wt % and less than or equal to 0.29 wt %.

In an embodiment, the amount of drug-polymer conjugate is greater than 0.1 wt % and less than or equal to 1 wt % or 2 wt %. In an embodiment, the amount of drug-polymer conjugate is greater than 0.1 wt % and less than or equal to 0.50 wt %. In an embodiment, the amount of drug-polymer conjugate is greater than 0.1 wt % and less than or equal to 0.40 wt %. In an embodiment, the amount of drug-polymer conjugate is greater than 0.1 wt % and less than or equal to 0.35 wt %. In an embodiment, the amount of drug-polymer conjugate is greater than 0.1 wt % and less than or equal to 0.30 wt %. In an embodiment, the amount of drug-polymer conjugate is greater than 0.1 wt % and less than or equal to 0.29 wt %.

Implantable Devices

All embodiments described herein are applicable to implantable medical devices, especially those that have load bearing portions when in use or have portions that undergo deformation during use. In particular, all embodiments are applicable to tubular implantable medical devices such as self-expandable stents, balloon-expandable stents, and stent-grafts. Such stents can have a scaffold body made from a material comprising polymer(s), metal(s), or a combination of polymer(s) and metal(s). The polymer and metal materials can be bioabsorbable and/or biostable. Preferably the materials are bioabsorbable such that the stent or scaffold bioabsorbs after a period of weeks, months, or years. The polymer(s) can comprise a PLA-based polymer described herein, a combination of PLA-based polymers described herein, or a combination of PLA-based polymer(s) described herein and other materials and/or polymers.

A stent or scaffold may include a tubular scaffold structure that is composed of a plurality of ring struts and link struts. The rings and struts can be polymeric, for example the rings and struts can comprise a PLA-based polymer or polymers described herein. The ring struts form a plurality of cylindrical rings arranged about the cylindrical axis. The rings are connected by the link struts. The links can also comprise, or consist essentially of, polymers. For example, the links can comprise, or consist essentially of, a PLA-based polymer or polymers described herein. The scaffold comprises an open framework or pattern of struts and links that define a generally tubular body with gaps in the body defined by the rings and struts. A scaffold corresponding to a stent body may be formed from a hollow cylindrical tube into this open framework of struts and links by laser cutting a pattern into a thin-walled tube that prior to cutting may have no gaps in the tube wall. Scaffold may refer to a coated or uncoated structure.

FIG. 1 depicts a view of an exemplary scaffold 100 which includes a pattern or network of interconnecting structural elements 105. FIG. 1 illustrates features that are typical to many stent patterns including cylindrical rings 107 connected by linking elements 110. The cylindrical rings are load bearing in that they provide radially directed force in response to an inward force on the scaffold. The linking elements generally function to hold the cylindrical rings together. Exemplary scaffolds are disclosed in US2008/0275537, US2011/0190872, and US2011/0190871.

A stent or scaffold, in some embodiments, may have lengths of between 8 and 18 mm, 18 and 36 mm, 36 and 40 mm, or between 40 and 200 mm as fabricated or when implanted in an artery. The dimensions of the scaffold may correspond to an as-cut condition, after coating the scaffold, or just prior to crimping (pre-crimped). Exemplary lengths include 8 mm, 12 mm, 14 mm, 18 mm, 24 mm, 28, and 48 mm. The scaffold may have a pre-crimping or as-fabricated diameter of between 1 and 2 mm, 2 and 3 mm, 2.5 and 3.5 mm, 3 and 4 mm, 3 and 5 mm, 5 and 10 mm, 6 and 8 mm, or any value between and including these endpoints. Diameter may refer to the inner diameter or outer diameter of the scaffold. Exemplary diameters include 2.5 mm, 3.0 mm, 3.25 mm, 3.5 mm, 4 mm, 5 mm, or 6 mm. The struts of scaffold may have a radial wall thickness and/or width of 150 microns, about 75 to 100 microns, about 100 to 150 microns, 150 to 200 microns, 200 to 250 microns, 250 to 300 microns, 300 to 350 microns, 350 to 400 microns, or greater than 400 microns.

The scaffold may be configured for being deployed by a non-compliant or semi-compliant balloon of 0.8 to 1 mm, 1 to 1.2 mm, 1.2 to 1.4 mm, 1.4 to 1.6 mm, 1.6 to 1.8 mm, and 1.8 to 2.2 mm, 1 mm, 1.2 mm, 1.3 mm, 1.4, mm, 1.6 mm, 1.8 mm, or 2 mm diameter crimped profile or diameter. Exemplary balloon sizes include 2.5 mm, 3 mm, 3.5 mm, 4 mm, 5.5 mm, 5 mm, 5.5 mm, 6 mm, 6.5 mm, 7 mm, and 8 mm, where the balloon size refers to a nominal inflated diameter of the balloon. The scaffold may be deployed to a diameter of between 2.5 mm and 3 mm, 3 mm and 3.5 mm, 3.5 mm and 4 mm, 4 mm and 10 mm, 7 and 9 mm, or any value between and including the endpoints. In certain embodiments, the scaffold is provided in a crimped diameter over, and in contact with, a deflated catheter balloon.

The fabrication of the stent or scaffold can include forming a hollow, thin-walled cylindrical tube. The tube may initially have no gaps or holes in its walls. A scaffold or patterned structure may be formed by laser cutting the tube. A pre-cut tube can be formed by extrusion, injection molding, dipping, or spraying.

A coating may be formed over the scaffold by mixing a coating polymer (e.g., a PLA-based polymer) and a drug (e.g., a macrocyclic drug) in a solvent (e.g., an organic solvent) and applying the solution to the surface of the scaffold. The application may be performed by spraying, dipping, ink-jet printing, or rolling the scaffold in the solution. The coating may be formed as a series of layers by spraying or dipping followed by a step to remove all or most of residual solvent via, for example, evaporation by heating. The steps may then be repeated until a desired coating thickness is achieved.

Manufacturing processes or standards can be set, adjusted, selected and/or determined such that the amount of drug conjugated to the polymer is controlled. In certain embodiments, the manufacturing processes that are set, adjusted and/or determined include one or a combination of spraying, dipping, annealing, drying, solvent selection, heating, sterilizing, crimping and packaging. In an embodiment, the manufacturing processes or standards are set, adjusted, selected and determined such that the amount of drug conjugated to the polymer is less than or equal to 0.35% (weight drug to weight polymer), as measured by liquid chromatography-mass spectrometry (LC-MS). For example, one of ordinary skill in the art, as part of routine experimentation, would be able to adjust parameters such as temperature and humidity such that the amount drug-polymer conjugate is sufficiently low so as not to decrease the drug dose from the device and not to generate new species with unknown biological and/or toxicological properties.

In certain embodiments, the solvent is an organic solvent. In certain embodiments, the solvent is an organic solvent selected from chloroform, acetone, dimethylsulfoxide, propylene glycol methyl ether, iso-propylalcohol, tetrahydrofuran, dimethylformamide, dimethyl acetamide, benzene, toluene, xylene, hexane, cyclohexane, heptane, octane, nonane, decane, decalin, ethyl acetate, butyl acetate, cyclohexanone, cyclohexanol, 1,4-dioxane, isobutyl acetate, isopropyl acetate, butanol, diacetone alcohol, benzyl alcohol, 2-butanone, dioxane, methylene chloride, carbon tetrachloride, tetrachloroethylene, tetrachloro ethane, chlorobenzene, 1,1,1-trichloroethane, formamide, hexafluoroisopropanol, 1,1,1-trifluoroethanol, hexamethyl phosphoramide, and a combination thereof.

The coated scaffold may then be crimped over a delivery balloon. The crimped scaffold may then be packaged and then sterilized with electron-beam (E-Beam) radiation or other forms of sterilization. The range of exposure may be between 20 and 30 kGy, 25 to 35 kGy, or 25 to 30 kGy.

Additionally, the fabrication of the scaffold can include processing that increases the strength of the scaffold body and also the radial strength of the scaffold. The processing may increase the crystallinity of the scaffold polymer which increases the strength and the radial strength of the scaffold. In another embodiment, the processing may increase the alignment of the scaffold polymer which increases the strength and radial strength of the scaffold. The processing can be performed prior to laser cutting, after laser cutting, or both.

The processing can include annealing the pre-cut tube and/or the scaffold at a temperature and for a time sufficient to increase the crystallinity to a desired level. The temperature may be between the glass transition temperature (Tg) of the scaffold polymer and the melting temperature (Tm) of the scaffold polymer.

Additionally or alternatively, the processing can include radially deforming the pre-cut tube to increase the radial strength of the tube. The radially expanded tube may then be laser cut to form a scaffold. The radial expansion increases the radial strength both through an increase in crystallinity and induced polymer chain alignment in the circumferential direction. The radial expansion process may be performed by a process such as blow molding. In blow molding, the pre-cut tube may be disposed within a mold and heated to a temperature between Tg and Tm and expanded by increasing a pressure inside of the tube.

The crystallinity of the pre-cut tube prior to the processing may be less than 5%, 1 to 5%, 5 to 10%, less than 10%, 10 to 15%, 15 to 30%, or less than 30%. In an embodiment, the crystallinity can be between 10-25%. The crystallinity of the processed tube, cut scaffold, crimped scaffold, sterilized scaffold, may be 20 to 30%, 20 to 25%, 30 to 40%, 40 to 45%, 45 to 50%, or greater than 50%.

The intended deployment diameter may correspond to, but is not limited to, the nominal deployment diameter of a catheter balloon which is configured to expand the scaffold. A device scaffold may be laser cut from a tube (i.e., a pre-cut tube) that is less than an intended deployment diameter. In this case, the pre-cut tube diameter may be 0.2 to 1 times the intended deployment diameter or any value in between and including the endpoints.

A scaffold may be laser cut from a tube (i.e., a pre-cut tube) that is greater than an intended deployment diameter. In this case, the pre-cut tube diameter may be 1 to 1.5 times the intended deployment diameter, or any value in between and including the endpoints.

The drug release rate may be controlled by adjusting the ratio of drug and polymeric coating material. The drug may be released from the coating over a period of one to two weeks, up to one month, or up to three months after implantation. In an embodiment, the drug is released from the coating over a period greater than three months. Thickness or average thickness of the coating on the device body may be less than 4 microns, 3 microns, or 2.5 microns. In some embodiments, the thickness or average thickness of the coating on the device body may be 1 to 20 microns, 1 to 2 microns, 2 to 3 microns, 2 to 2.9 microns, 2 to 2.5 microns, 1 to 3 microns, 2 to 5 microns, 3 to 5 microns, 5 to 10 microns, or 10 to 20 microns. The coating may be over part of the surface or the entire surface of a scaffold substrate. In some embodiments, the body of the device includes a drug release coating and the body is free of drug, aside from any incidental migration of drug into the body from the coating.

In some embodiments, the coating may include a primer layer between the scaffold body or structure and a drug delivery coating layer to enhance the adhesion of the drug coating to the scaffold. Alternatively, the coating may have no primer layer and only a drug delivery coating layer.

Embodiments also include the coating on a metallic stent or scaffold. The metallic scaffold can be bioerodible or nonbioerodible. Exemplary metals include cobalt chromium, stainless steel, or nickel titanium alloy. The thickness or width of the struts of a metallic stent may be 70 to 100 microns, 75 to 85 microns, 78 microns, 80 microns, or 81 microns.

The terms bioresorbable, biodegradable, bioabsorbable, and bioerodable are used interchangeably and refer to polymers that are capable of being degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. Tg of a given polymer can be dependent on the heating rate and can be influenced by the thermal history of the polymer as well as its degree of crystallinity. Furthermore, the chemical structure of the polymer heavily influences the glass transition by affecting mobility.

The Tg can be determined as the approximate midpoint of a temperature range over which the glass transition takes place. See, ASTM standard D883-90. The most frequently used definition of Tg uses the energy release on heating in differential scanning calorimetry (DSC). As used herein, the Tg refers to a glass transition temperature as measured by differential scanning calorimetry (DSC) at a 20° C./min heating rate.

The "melting temperature" (Tm) is the temperature at which a material changes from solid to liquid state. In polymers, Tm is the peak temperature at which a semicrystalline phase melts into an amorphous state. Such a melting process usually takes place within a relative narrow range (<20° C.), thus it is acceptable to report Tm as a single value.

Implantable Devices Comprising Drug-PLA Polymer Conjugate

In an aspect, provided herein is an implantable device, for example a stent or bioabsorbable scaffold, comprising a device body and a coating on the device body, the coating comprising a poly(D,L-lactide) (PDLLA) polymer and a drug conjugated to the polymer, wherein the amount of drug conjugated to the polymer is less than or equal to 0.35% (weight drug to weight polymer), as measured by liquid chromatography-mass spectrometry (LC-MS). In an embodiment, the drug is biolimus, merilimus, myolimus, novolimus, paclitaxel, pimecrolimus, 16-pent-2-ynyloxy-32(S)-dihydro-rapamycin, ridaforolimus, sirolimus, tacrolimus, temsirolimus or zotarolimus. In an embodiment, the drug is a macrocyclic drug. In an embodiment, the drug is novolimus.

In an aspect, provided herein is an implantable device, for example a stent or bioabsorbable scaffold, comprising a device body and a coating on the device body, the coating comprising a polymer, wherein the polymer comprises a lactide or lactic acid based polymer and a drug conjugated to the lactide or lactic acid based polymer, wherein the amount of drug conjugated to the polymer is less than or equal to 0.35% (weight drug to weight polymer). In an embodiment, the amount of drug-polymer conjugate is as measured by liquid chromatography-mass spectrometry (LC-MS). In an embodiment, the amount of drug-polymer conjugate is as measured by Gel Permeation Chromatography with Refractive Index and Ultraviolet detection (GPC-RI/UV). In an embodiment, the drug is a macrocyclic drug. In an embodiment, the drug is biolimus, merilimus, myolimus, novolimus, paclitaxel, pimecrolimus, 16-pent-2-ynyloxy-32(S)-dihydro-rapamycin, ridaforolimus, sirolimus, tacrolimus, temsirolimus or zotarolimus. In an embodiment, the drug is novolimus.

In another embodiment, provided herein is an implantable device, for example a stent or a bioabsorbable scaffold, comprising a device body and a coating on the device body, the coating comprising a polymer, wherein the polymer comprises a lactide, lactide units, a lactic acid, or lactic acid units and a drug conjugated to the lactide, lactide units, lactic acid, or lactic acid units, wherein the amount of drug conjugated to the polymer is less than or equal to 0.35% (weight drug to weight polymer), as measured by liquid chromatography-mass spectrometry (LC-MS). In an embodiment, the amount of drug-polymer conjugate is as measured by Gel Permeation Chromatography with Refractive Index and Ultraviolet detection (GPC-RI/UV). In an embodiment, the drug is a macrocyclic drug. In an embodiment, the drug is biolimus, merilimus, myolimus, novolimus, paclitaxel, pimecrolimus, 16-pent-2-ynyloxy-32(S)-dihydro-rapamycin, ridaforolimus, sirolimus, tacrolimus, temsirolimus or zotarolimus. In an embodiment, the drug is novolimus.

In an aspect, provided herein is a method of manufacturing an implantable device, for example a stent or bioabsorbable scaffold, comprising a device body and a coating on the device body, the coating comprising a poly(D,L-lactide) (PDLLA) polymer and a drug conjugated to the polymer, wherein the manufacturing processes or standards are set, adjusted, selected and/or determined such that the amount of drug conjugated to the polymer is less than or equal to 0.35% (weight drug to weight polymer). In an embodiment, the amount of drug-polymer conjugate is as measured by liquid chromatography-mass spectrometry (LC-MS). In an embodiment, the amount of drug-polymer conjugate is as measured by Gel Permeation Chromatography with Refractive Index and Ultraviolet detection (GPC-RI/UV). In certain embodiments, the manufacturing processes that are set, adjusted and/or determined include one or a combination of spraying, dipping, annealing, drying, solvent selection, heating, sterilizing, crimping and/or packaging. In an embodiment, the drug is biolimus, merilimus, myolimus, novolimus, paclitaxel, pimecrolimus, 16-pent-2-ynyloxy-32(S)-dihydro-rapamycin, ridaforolimus, sirolimus, tacrolimus, temsirolimus or zotarolimus. In an embodiment, the drug is a macrocyclic drug. In an embodiment, the drug is novolimus.

In an aspect, provided herein is a method of manufacturing an implantable device, for example a stent or bioabsorbable scaffold, comprising a device body and a coating on the device body, the coating comprising a lactide or lactic acid based polymer and a drug conjugated to the polymer, wherein the manufacturing processes or standards are set, adjusted, selected and/or determined such that the amount of drug conjugated to the polymer is less than or equal to 0.35% (weight drug to weight polymer). In an embodiment, the amount of drug-polymer conjugate is as measured by liquid chromatography-mass spectrometry (LC-MS). In an embodiment, the amount of drug-polymer conjugate is as measured by Gel Permeation Chromatography with Refractive Index and Ultraviolet detection (GPC-RI/UV). In an embodiment, the drug is biolimus, merilimus, myolimus, novolimus, paclitaxel, pimecrolimus, 16-pent-2-ynyloxy-32(S)-dihydro-rapamycin, ridaforolimus, sirolimus, tacrolimus, temsirolimus or zotarolimus. In an embodiment, the drug is a macrocyclic drug. In an embodiment, the drug is novolimus.

In certain embodiments, the amount of drug conjugated to the polymer is less than or equal to 0.35% (weight drug to weight polymer), as measured by liquid chromatography-mass spectrometry (LC-MS). In certain embodiments, the amount of drug conjugated to the polymer is less than or equal to 0.1% (weight drug to weight polymer), as measured by gel permeation chromatography with refractive index and ultraviolet detection (GPC-RI/UV). In an embodiment, the drug is biolimus, merilimus, myolimus, novolimus, paclitaxel, pimecrolimus, 16-pent-2-ynyloxy-32(S)-dihydro-rapamycin, ridaforolimus, sirolimus, tacrolimus, temsirolimus or zotarolimus. In an embodiment, the drug is a macrocyclic drug. In an embodiment, the drug is novolimus.

In the embodiments described herein, the coating comprises a majority percentage of the drug which is not conjugated to the polymer. In an embodiment, the non-conjugated drug is blended, mixed or disbursed with the polymer. In an embodiment, the non-conjugated drug is blended, mixed or disbursed with the polymer as fine particles. In an embodiment, the non-conjugated drug exists as drug rich domains dispersed in a polymer rich phase. In an embodiment, the non-conjugated drug is completely blended, mixed or disbursed throughout the polymer. In an embodiment, the drug is biolimus, merilimus, myolimus, novolimus, paclitaxel, pimecrolimus, 16-pent-2-ynyloxy-32(S)-dihydro-rapamycin, ridaforolimus, sirolimus, tacrolimus, temsirolimus or zotarolimus. In an embodiment, the drug is a macrocyclic drug. In an embodiment, the drug is novolimus.

In certain embodiments, the device body itself comprises poly(L-lactide) (PLLA). In certain embodiments, the device body comprises poly(D,L-lactide) (PDLLA) having a constitutional unit weight-to-weight (wt/wt) ratio of about 96/4. The device body can be made of a PLLA based polymer. The device body can be made of a PLA-based polymer. The device body itself can be made from a polymer having lactide or lactic acid units. In some embodiments, an implantable device described herein (for example a PLA-based stent or bioabsorbable scaffold, a PLLA based stent or bioabsorbable scaffold, or a lactide/lactic acid based stent or bioabsorbable scaffold) is designed to bioerode within a timeframe of 4 months to 3 years after device delivery, preferably from 5 months to 2 years after device delivery. In an embodiment, the drug is biolimus, merilimus, myolimus, novolimus, paclitaxel, pimecrolimus, 16-pent-2-ynyloxy-32(S)-dihydro-rapamycin, ridaforolimus, sirolimus, tacrolimus, temsirolimus or zotarolimus. In an embodiment, the drug is a macrocyclic drug. In an embodiment, the drug is novolimus.

In certain embodiments, the drug is conjugated to the polymer via an ester linkage. In an embodiment, the drug is biolimus, merilimus, myolimus, novolimus, paclitaxel, pimecrolimus, 16-pent-2-ynyloxy-32(S)-dihydro-rapamycin, ridaforolimus, sirolimus, tacrolimus, temsirolimus or zotarolimus. In an embodiment, the drug is a macrocyclic drug. In an embodiment, the drug is novolimus.

In certain embodiments, a drug-polymer conjugate is present in a finished product. As used herein, "finished product" includes an implantable device or scaffold as described herein after sterilization, for example after gamma radiation sterilization by or after electron beam sterilization. The term "finished product" also includes an implantable device or scaffold as described herein which has been sterilized and packaged. The term "finished product" also includes an implantable device or scaffold as described herein which has been sterilized and inserted into a patient.

In an aspect, provided herein is a method of treating restenosis, vulnerable plaque, or a vascular condition in a mammal comprising delivering a device described herein to the mammal. In certain embodiments, the device absorbs away anywhere from 5 months to 2 years after delivery.

EXAMPLE

An implantable device comprising a macrocyclic drug-PLA polymer conjugate is fabricated and tested as described in the following prophetic example.

Implantable Device

A scaffold comprised of a bioresorbable polymer is made by manipulating the polymer form a tube at a temperature above its melting point, followed by machining the scaffold pattern using a laser. The scaffold pattern itself is multilink composed of a series of corrugated rings joined by links.

Polymer

A PLA-based polymer, such as pure poly(L-lactide), poly(L-lactide-co-D,L-lactide), or poly(L-lactide-co-caprolactone), is used for the scaffold. Where D,L-lactide or caprolactone are present, preferred amounts are 1 to 10% (w/w). A poly(L-lactide) polymer with an inherent viscosity of 2.0-5.0 dL/gm can also be used. A coronary scaffold is fabricated with strut thickness and strut width in the range of 100-175 microns.

Coating Layer

Placed onto the scaffold is a coating composed of a bioresorbable polymer and a macrocyclic drug. The bioresorbable polymer may be poly(L-lactide), poly(D,L-lactide), poly(D,L-lactide-co-glycolide), poly(lactide-co-caprolactone), poly(D,L-lactide-co-caprolactone), poly(glycolide-co-caprolactone), or poly(L-lactide-co-glycolide). It is preferred for the degree of crystallinity of the polymer in the coating to be less than 25% to facilitate drug release. It is also preferred that the number average molecular weight ($M_n$) of the polymer in the coating be from 20,000 Da to 60,000 Da. The coating may be conformal, covering all strut surfaces, or it may be primarily abluminal, with only a portion on the strut sidewalls. For example, a macrocyclic drug is combined with poly(D,L-lactide) and spray coated in a conformal manner onto the scaffold at a drug dose density of 50-150 $\mu g/cm^2$ of scaffold surface area. In a preferred embodiment the drug is novolimus.

Amount of Conjugate in Coating

Following device assembly by attachment of the scaffold to the delivery catheter, it is packaged and terminally sterilized via e-beam radiation or gamma radiation. A preferred embodiment utilizes radiation sterilization at a dose of 15-35 kGy. In the finished device, the amount of drug-polymer conjugate present is less than 0.35% (w/w) as measured by LC-MS.

Amount of Novolimus in Coating

For novolimus, a preferred dose range is 2-8 µg/mm stent length, with 3-7 µg/mm most preferred, and 4-6 µg/mm especially preferred. Useful drug:polymer ratios are those which allow for the controlled released of the drug. Too low of a drug:polymer ratio and the drug will tend to be trapped and not release until substantial polymer degradation occurs. Too high of a drug:polymer ratio leads to rapid drug release. Preferred ranges of drug:polymer ratio are 1:2 to 2:1 by weight. A preferred ratio of novolimus to poly(D,L-lactide) is 1:1 by weight.

Detecting Amount of Conjugate in Coating

Scaffold samples are extracted with acetonitrile and analyzed for novolimus and related species using a LC-MS system. LC-MS analyses are performed using a Thermo Surveyor HPLC in tandem with TSQ Quantum Discovery mass spectrometer with an electrospray ionization (ESI) source. Chromatographic separation is achieved on a reversed-phase HPLC column (Hypersil-Keystone BDS, C18, 5 µm, 250×3.0 mm) using a gradient mobile phase of potassium dihydrogen phosphate (2 mM) with 0.005 mM sodium azide and acetonitrile. Flow rate is 1.1 mL/min, with a column temperature of 50° C., a sample temperature of 5° C., and an injection volume of 40 µL. The UV detector is set at 277 nm and used to monitor the separation. The HPLC eluent is then introduced to the mass spectrometer for mass detection. The ESI is operated in positive ionization mode and the mass spectrometer set to scan a mass to charge ratio (m/z) from 400 to 1,400 amu. Novolimus is detected as a singly charged ion with ammonium adduct. Novolimus conjugated to lactic acid, novolimus conjugated to lactic acid dimer, and novolimus conjugated to PLA oligomers are detected at the expected mass-to-charge (m/z) ratios.

The following are non-limiting embodiments of the drug delivery devices described herein.

Embodiment 1

A bioabsorbable scaffold comprising a scaffold body and a coating on the scaffold body, the coating comprising a poly(D,L-lactide) polymer and novolimus conjugated to the polymer, wherein the amount of novolimus conjugated to the polymer is less than or equal to 0.35% (weight novolimus to weight polymer), as measured by liquid chromatography-mass spectrometry (LC-MS).

Embodiment 2

The bioabsorbable scaffold of embodiment 1, wherein the amount of novolimus conjugated to the polymer is less than or equal to 0.30% (weight novolimus to weight polymer), as measured by liquid chromatography-mass spectrometry (LC-MS).

Embodiment 3

The bioabsorbable scaffold of embodiment 1 or 2, wherein the amount of novolimus conjugated to the polymer is less than or equal to 0.1% (weight novolimus to weight polymer), as measured by Gel Permeation Chromatography with Refractive Index and Ultraviolet detection (GPC-RI/UV).

Embodiment 4

The bioabsorbable scaffold of any of embodiments 1-3, wherein the coating comprises novolimus which is not conjugated to the polymer.

Embodiment 5

The bioabsorbable scaffold of any of embodiments 1-4, wherein the scaffold body comprises a PLA-based polymer.

Embodiment 6

The bioabsorbable scaffold of any of embodiments 1-4, wherein the scaffold body comprises poly(L-lactide) (PLLA).

Embodiment 7

The bioabsorbable scaffold of any of embodiments 1-4, wherein the scaffold body comprises poly(L-lactide-co-caprolactone).

Embodiment 8

The bioabsorbable scaffold of any of embodiments 1-4, wherein the scaffold body comprises poly(D,L-lactide) (PDLLA).

Embodiment 9

The bioabsorbable scaffold of any of embodiments 1-8, wherein the novolimus is conjugated to the polymer via an ester linkage.

Embodiment 10

A bioabsorbable scaffold comprising a scaffold body and a coating on the scaffold body, the coating comprising a polymer, wherein the polymer comprises a lactide or lactic acid based polymer and novolimus conjugated to the lactide or lactic acid based polymer, wherein the amount of novolimus conjugated to the polymer is less than or equal to 0.35% (weight novolimus to weight polymer), as measured by liquid chromatography-mass spectrometry (LC-MS).

Embodiment 11

The bioabsorbable scaffold of embodiment 10, wherein the amount of novolimus conjugated to the polymer is less than or equal to 0.30% (weight novolimus to weight polymer), as measured by liquid chromatography-mass spectrometry (LC-MS).

Embodiment 12

The bioabsorbable scaffold of embodiment 10 or 11, wherein the amount of novolimus conjugated to the polymer is less than or equal to 0.1% (weight novolimus to weight polymer), as measured by Gel Permeation Chromatography with Refractive Index and Ultraviolet detection (GPC-RI/UV).

Embodiment 13

The bioabsorbable scaffold of any of embodiments 10-12, wherein the polymer comprises L-lactide or D-lactide.

Embodiment 14

The bioabsorbable scaffold of any of embodiments 10-13, wherein the scaffold body comprises a PLA-based polymer.

Embodiment 15

The bioabsorbable scaffold of any of embodiments 10-13, wherein the scaffold body comprises PLLA.

Embodiment 16

The bioabsorbable scaffold of any of embodiments 10-13, wherein the scaffold body comprises poly(L-lactide-co-caprolactone).

Embodiment 17

The bioabsorbable scaffold of any of embodiments 10-13, wherein the scaffold body comprises PDLLA.

Embodiment 18

The bioabsorbable scaffold of any of embodiments 10-17, wherein the novolimus is conjugated to the polymer via an ester linkage.

Embodiment 19

An implantable device comprising a device body and a coating on the device body, the coating comprising a polymer, wherein the polymer comprises a lactide, lactide units, a lactic acid, or lactic acid units and novolimus conjugated to the lactide, lactide units, lactic acid, or lactic acid units, wherein the amount of novolimus conjugated to the polymer is less than or equal to 0.35% (weight novolimus to weight polymer), as measured by liquid chromatography-mass spectrometry (LC-MS).

Embodiment 20

The implantable device of embodiment 19, wherein the amount of novolimus conjugated to the polymer is less than or equal to 0.30% (weight novolimus to weight polymer), as measured by liquid chromatography-mass spectrometry (LC-MS).

Embodiment 21

The implantable device of embodiment 19 or 20, wherein the amount of novolimus conjugated to the polymer is less than or equal to 0.1% (weight novolimus to weight polymer), as measured by Gel Permeation Chromatography with Refractive Index and Ultraviolet detection (GPC-RI/UV).

Embodiment 22

The implantable device of any of embodiments 19-21, wherein the polymer comprises L-lactide or D-lactide.

Embodiment 23

The implantable device of any of embodiments 19-22, wherein the scaffold body comprises a PLA-based polymer.

Embodiment 24

The implantable device of any of embodiments 19-22, wherein the scaffold body comprises PLLA.

Embodiment 25

The implantable device of any of embodiments 19-22, wherein the scaffold body comprises PDLLA.

Embodiment 26

The implantable device of any of embodiments 19-22, wherein the scaffold body comprises poly(L-lactide-co-caprolactone).

Embodiment 27

The implantable device of any of embodiments 19-26, wherein the novolimus is conjugated to the polymer via an ester linkage.

Embodiment 28

The implantable device of any of embodiments 19-27, wherein the coating comprises a polymer selected from the group consisting of poly(L-lactide), poly(D-lactide), poly(D,L-lactide), poly(L-lactide-co-D,L-lactide), poly(L-lactide-co-glycolide), poly(D,L-lactide-co-glycolide), poly(L-lactide-co-caprolactone), poly(D,L-lactide-co-caprolactone), poly(D,L-lactide) made from meso-lactide, poly(D,L-lactide) made from polymerization of a racemic mixture of L- and D-lactides, and a combination thereof.

Embodiment 29

The implantable device of any of embodiments 19-28, wherein the coating comprises a polymer having a number average molecular weight selected over the range of 20,000 Da to 60,000 Da.

Embodiment 30

A method of manufacturing a bioabsorbable scaffold comprising forming a scaffold body and a coating on the scaffold body, the coating comprising a poly(D,L-lactide) polymer and novolimus conjugated to the polymer, wherein the manufacturing processes or standards are set, adjusted, selected and/or determined such that the amount of novolimus conjugated to the polymer is less than or equal to 0.35% (weight novolimus to weight polymer), as measured by liquid chromatography-mass spectrometry (LC-MS).

Embodiment 31

The method of embodiment 30, wherein the amount of novolimus conjugated to the polymer is less than or equal to 0.30% (weight novolimus to weight polymer), as measured by liquid chromatography-mass spectrometry (LC-MS).

Embodiment 32

The method of embodiment 30 or 31, wherein the amount of novolimus conjugated to the polymer is less than or equal to 0.1% (weight novolimus to weight polymer), as measured by Gel Permeation Chromatography with Refractive Index and Ultraviolet detection (GPC-RI/UV).

Embodiment 33

The method of any of embodiments 30-32, wherein the coating comprises novolimus which is not conjugated to the polymer.

Embodiment 34

The method of any of embodiments 30-33, wherein the scaffold body comprises a PLA-based polymer.

Embodiment 35

The method of any of any of embodiments 30-33, wherein the scaffold body comprises PLLA.

Embodiment 36

The method of any of any of embodiments 30-33, wherein the scaffold body comprises PDLLA.

Embodiment 37

The method of any of any of embodiments 30-33, wherein the scaffold body comprises poly(L-lactide-co-caprolactone).

Embodiment 38

The method of any of any of embodiments 30-37, wherein the coating comprises a polymer having a number average molecular weight selected over the range of 20,000 Da to 60,000 Da.

Embodiment 39

The method of any of embodiments 30-38, wherein the novolimus is conjugated to the polymer via an ester linkage.

Embodiment 40

The method of any of embodiments 30-39, wherein the manufacturing processes or standards that are set, adjusted, selected and/or determined include one or a combination of solvent selection, drug and polymer dissolution parameters, spraying parameters, dipping parameters, inkjet printing parameters, annealing parameters, drying parameters, heating parameters, crimping parameters, sterilizing parameters, packaging, temperature, and/or humidity.

Embodiment 41

A method of manufacturing a bioabsorbable scaffold comprising forming a scaffold body and a coating on the scaffold body, the coating comprising a lactide or lactic acid based polymer and novolimus conjugated to the polymer, wherein the manufacturing processes or standards are set, adjusted, selected and/or determined such that the amount of novolimus conjugated to the polymer is less than or equal to 0.35% (weight novolimus to weight polymer).

Embodiment 42

The method of embodiment 41, wherein the amount of novolimus conjugated to the polymer is less than or equal to 0.30% (weight novolimus to weight polymer), as measured by liquid chromatography-mass spectrometry (LC-MS).

Embodiment 43

The method of any of embodiments 41-42, wherein the amount of novolimus conjugated to the polymer is less than or equal to 0.1% (weight novolimus to weight polymer), as measured by Gel Permeation Chromatography with Refractive Index and Ultraviolet detection (GPC-RI/UV).

Embodiment 44

The method of any of embodiments 41-43, wherein the coating comprises novolimus which is not conjugated to the polymer.

Embodiment 45

The method of any of embodiments 41-44, wherein the polymer comprises L-lactide or D-lactide.

Embodiment 46

The method of any of embodiments 41-45, wherein the scaffold body comprises a PLA-based polymer.

Embodiment 47

The method of any of embodiments 41-45, wherein the scaffold body comprises PLLA.

Embodiment 48

The method of any of embodiments 41-45, wherein the scaffold body comprises PDLLA.

Embodiment 49

The method of any of embodiments 41-45, wherein the scaffold body comprises poly(L-lactide-co-caprolactone).

Embodiment 50

The method of any of any of embodiments 41-49, wherein the coating comprises a polymer selected from the group consisting of poly(L-lactide), poly(D-lactide), poly(D,L-lactide), poly(L-lactide-co-D,L-lactide), poly(L-lactide-co-glycolide), poly(D,L-lactide-co-glycolide), poly(L-lactide-co-caprolactone), poly(D,L-lactide-co-caprolactone), poly(D,L-lactide) made from meso-lactide, poly(D,L-lactide) made from polymerization of a racemic mixture of L- and D-lactides, and a combination thereof.

Embodiment 51

The method of any of any of embodiments 41-50, wherein the coating comprises a polymer having a number average molecular weight selected over the range of 20,000 Da to 60,000 Da.

Embodiment 52

The method of any of embodiments 41-51, wherein the novolimus is conjugated to the polymer via an ester linkage.

Embodiment 53

The method of any of embodiments 41-52, wherein the manufacturing processes or standards that are set, adjusted, selected and/or determined include one or a combination of solvent selection, drug and polymer dissolution parameters, spraying parameters, dipping parameters, inkjet printing parameters, annealing parameters, drying parameters, heating parameters, crimping parameters, sterilizing parameters, packaging, temperature, and/or humidity.

Embodiment 54

A method of treating restenosis, vulnerable plaque, or a vascular condition in a mammal comprising delivering the scaffold of any of embodiments 1-53 to the mammal.

Embodiment 55

The method of embodiment 54, wherein the scaffold absorbs away anywhere from 5 months to 2 years after delivery.

All publications, patents, and patent applications cited in this specification are herein incorporated by reference as if each individual publication, patent, or patent application were specifically and individually indicated to be incorporated by reference. The following United States Provisional Patent Application is specifically incorporated by reference herein: U.S. 61/935,832 entitled "DRUG ELUTING SCAFFOLD OR STENT WITH A NOVOLIMUS AND LACTIDE BASED COATING SUCH THAT NOVOLIMUS HAS A MINIMUM/INSIGNIFICANT AMOUNT OF BONDING TO THE COATING" filed 4 Feb. 2014.

While the claimed subject matter has been described in terms of various embodiments, the skilled artisan will appreciate that various modifications, substitutions, omissions, and changes may be made without departing from the spirit thereof. Accordingly, it is intended that the scope of the claimed subject matter is limited solely by the scope of the following claims, including equivalents thereof.

What is claimed is:

1. A method of treating restenosis, vulnerable plaque, or a vascular condition in a mammal comprising delivering to the mammal a bioabsorbable scaffold comprising a scaffold body and a coating on the scaffold body, the coating comprising a polymer, wherein the polymer comprises a lactide or lactic acid based polymer and novolimus conjugated to the lactide or lactic acid based polymer in an amount, wherein the amount of novolimus conjugated to the polymer is less than or equal to 0.35% (weight novolimus to weight polymer), as measured by liquid chromatography-mass spectrometry (LC-MS); wherein conjugation of the novolimus to the polymer includes conjugation via an ester linkage.

2. The method of claim 1, wherein the bioabsorbable scaffold absorbs away anywhere from 5 months to 2 years after delivery.

3. A method of manufacturing a bioabsorbable scaffold comprising forming a scaffold body and a coating on the scaffold body, the coating comprising a poly(D,L-lactide) polymer and novolimus conjugated to the polymer in an amount, wherein the manufacturing processes or standards are set, adjusted, selected and/or determined such that the amount of novolimus conjugated to the polymer is less than or equal to 0.35% (weight novolimus to weight polymer), as measured by liquid chromatography-mass spectrometry (LC-MS); wherein conjugation of the novolimus to the polymer includes conjugation via an ester linkage.

4. The method of claim 3, wherein the amount of novolimus conjugated to the polymer is less than or equal to 0.30% (weight novolimus to weight polymer), as measured by liquid chromatography-mass spectrometry (LC-MS).

5. The method of claim 3, wherein the amount of novolimus conjugated to the polymer is less than or equal to 0.1%

(weight novolimus to weight polymer), as measured by Gel Permeation Chromatography with Refractive Index and Ultraviolet detection (GPC-RI/UV).

6. The method of claim 3, wherein the coating comprises novolimus which is not conjugated to the polymer.

7. The method of claim 3, wherein the manufacturing processes or standards that are set, adjusted, selected and/or determined include one or a combination of solvent selection, drug and polymer dissolution parameters, spraying parameters, dipping parameters, inkjet printing parameters, annealing parameters, drying parameters, heating parameters, crimping parameters, sterilizing parameters, packaging, temperature, and/or humidity.

8. A method of treating restenosis, vulnerable plaque, or a vascular condition in a mammal comprising delivering the bioabsorbable scaffold of claim 3 to the mammal.

9. The method of claim 8, wherein the bioabsorbable scaffold absorbs away anywhere from 5 months to 2 years after delivery.

10. A method of manufacturing a bioabsorbable scaffold comprising forming a scaffold body and a coating on the scaffold body, the coating comprising a lactide or lactic acid based polymer and novolimus conjugated to the polymer in an amount, wherein the manufacturing processes or standards are set, adjusted, selected and/or determined such that the amount of novolimus conjugated to the polymer is less than or equal to 0.35% (weight novolimus to weight polymer), as measured by liquid chromatography-mass spectrometry (LC-MS); wherein conjugation of the novolimus to the polymer includes conjugation via an ester linkage.

11. The method of claim 10, wherein the amount of novolimus conjugated to the polymer is less than or equal to 0.30% (weight novolimus to weight polymer), as measured by liquid chromatography-mass spectrometry (LC-MS).

12. The method of any of claim 10, wherein the amount of novolimus conjugated to the polymer is less than or equal to 0.1% (weight novolimus to weight polymer), as measured by Gel Permeation Chromatography with Refractive Index and Ultraviolet detection (GPC-RI/UV).

13. The method of claim 10, wherein the coating comprises novolimus which is not conjugated to the polymer.

14. The method of claim 10, wherein the manufacturing processes or standards that are set, adjusted, selected and/or determined include one or a combination of solvent selection, drug and polymer dissolution parameters, spraying parameters, dipping parameters, inkjet printing parameters, annealing parameters, drying parameters, heating parameters, crimping parameters, sterilizing parameters, packaging, temperature, and/or humidity.

15. A method of treating restenosis, vulnerable plaque, or a vascular condition in a mammal comprising delivering the bioabsorbable scaffold of claim 10 to the mammal.

16. The method of claim 15, wherein the bioabsorbable scaffold absorbs away anywhere from 5 months to 2 years after delivery.

17. The method of claim 1 wherein the amount of novolimus conjugated to the polymer is greater than 0.01 wt % and less than or equal to 0.35% (weight novolimus to weight polymer), as measured by liquid chromatography-mass spectrometry (LC-MS).

18. The method of claim 3 wherein the amount of novolimus conjugated to the polymer is greater than 0.01 wt % and less than or equal to 0.35% (weight novolimus to weight polymer), as measured by liquid chromatography-mass spectrometry (LC-MS).

19. The method of claim 10 wherein the amount of novolimus conjugated to the polymer is greater than 0.01 wt % and less than or equal to 0.35% (weight novolimus to weight polymer), as measured by liquid chromatography-mass spectrometry (LC-MS).

* * * * *